(12) United States Patent
Yang et al.

(10) Patent No.: US 8,877,792 B2
(45) Date of Patent: *Nov. 4, 2014

(54) COMPOSITIONS FOR INCREASING SOLUBILITY OF AZOLE DRUG COMPOUNDS THAT ARE POORLY SOLUBLE IN WATER

(71) Applicant: Dow Pharmaceutical Sciences, Inc., Petaluma, CA (US)

(72) Inventors: Meidong Yang, Richmond, CA (US); Haigang Chen, Edina, MT (US)

(73) Assignee: Dow Pharmaceutical Sciences, Inc., Petaluma, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/855,034

(22) Filed: Apr. 2, 2013

(65) Prior Publication Data

US 2013/0217742 A1    Aug. 22, 2013

Related U.S. Application Data

(63) Continuation of application No. 12/928,306, filed on Dec. 8, 2010, now Pat. No. 8,658,678, which is a continuation of application No. 12/012,413, filed on Feb. 2, 2008, now Pat. No. 7,893,097.

(51) Int. Cl.

| | | |
|---|---|---|
| *A61K 31/415* | (2006.01) | |
| *A61K 47/08* | (2006.01) | |
| *A61K 9/06* | (2006.01) | |
| *A61K 47/10* | (2006.01) | |
| *A61K 31/44* | (2006.01) | |
| *A61K 31/4164* | (2006.01) | |
| *A61K 47/26* | (2006.01) | |
| *A61K 9/00* | (2006.01) | |
| *A61K 9/10* | (2006.01) | |

(52) U.S. Cl.
CPC ............. *A61K 47/10* (2013.01); *A61K 47/26* (2013.01); *A61K 47/08* (2013.01); *A61K 9/06* (2013.01); *A61K 31/44* (2013.01); *A61K 9/0034* (2013.01); *A61K 31/4164* (2013.01); *A61K 31/415* (2013.01); *A61K 9/0014* (2013.01); *A61K 9/10* (2013.01)
USPC .................................. 514/396; 514/398

(58) Field of Classification Search
USPC .................................... 514/396, 398
See application file for complete search history.

(56) References Cited

U.S. PATENT DOCUMENTS

| | | |
|---|---|---|
| 6,294,192 B1 | 9/2001 | Patel |
| 6,395,765 B1 | 5/2002 | Etchegaray |
| 6,468,989 B1 | 10/2002 | Chang |
| 6,881,726 B2 | 4/2005 | Chang |
| 8,658,678 B2 * | 2/2014 | Yang et al. ............... 514/365 |

FOREIGN PATENT DOCUMENTS

WO    WO 2008/156798 A1    12/2008

OTHER PUBLICATIONS

Jokipii, L, "Comparative Evaluation of the 2-Methyl-5-Nitroimidazole Compounds Dimetridazole, Metronidazole, . . . ", Antimicrobial Agents and Chemotherapy, 28(4):561-564 (1985).

\* cited by examiner

*Primary Examiner* — Kevin E Weddington
(74) *Attorney, Agent, or Firm* — Kilpatrick Townsend & Stockton LLP

(57) ABSTRACT

The combination of any two of a polyol, a polyol ether, and a low carbon organic alcohol provides a synergistic effect on the solubility of azole compounds, such as metronidazole, in aqueous fluid.

10 Claims, No Drawings

COMPOSITIONS FOR INCREASING SOLUBILITY OF AZOLE DRUG COMPOUNDS THAT ARE POORLY SOLUBLE IN WATER

This application is a continuation of U.S. patent application Ser. No. 12/928,306, filed Dec. 8, 2010, now U.S. Pat. No. 8,658,678, which is a continuation of U.S. patent application Ser. No. 12/012,413, filed Feb. 2, 2008, now U.S. Pat. No. 7,893,097.

FIELD OF THE INVENTION

The present invention pertains to the field of increasing solubility of chemical compounds in aqueous fluids.

BACKGROUND OF THE INVENTION

Many chemical compounds, particular chemical compounds that are useful in pharmacologic applications, are poorly soluble in water. Such drugs may be classified according to USP-NF as being sparingly soluble, slightly soluble, very slightly soluble, or insoluble in water. Many of these compounds are also poorly soluble in oils. Au example of such a chemical compound includes the azole family of drugs, which family includes metronidazole, fluconazole, ketoconazole, itraconazole, miconazole, dimetridazole, secnidazole, ornidazole, tinidazole, carnidazole, and panidazole.

In many situations, such drugs may be formulated as a suspension, in which case the lack of solubility of the drug in water and in pharmaceutical oils does not typically have a negative impact on bioavailability. However, in situations where a solution of the drug is desired, or where an emulsion containing the drug in solution either in the hydrophilic or lipophilic phase of the emulsion is desired, the lack of solubility of the drug, in water and oils provides a significant obstacle to obtaining desired concentrations of the drug.

The need to increase the aqueous solubility of poorly water soluble drugs that are also poorly soluble in oils is especially critical when formulating an emulsion, such as a topical cream, lotion, or ointment, containing such a drug. In this case, in order to obtain a sufficiently high concentration of the drug in the emulsion formulation as a whole, the concentration of the drug, in the aqueous phase must be sufficiently elevated to overcome the lack of partitioning of the drug into the oil phase.

Metronidazole is an antimicrobial drug that is administered systemically for treatment of infections with anaerobic bacteria and protozoans, such as *Trichomonas, Entamoeba*, and *Giardia*. It is also used topically to treat bacterial vaginosis and various forms of acne, including acne rosacea. The aqueous solubility of metronidazole in water at room temperature is only about 0.87% w/w. Additionally, physically stable solutions of metronidazole in water that can withstand exposure to cold temperatures encountered during shipping are limited to about 0.7% w/w metronidazole. However for many topical applications, a concentration of 1.0% or higher is desired.

The lack of solubility of such drugs, and the inability to obtain sufficiently high concentrations of drugs in solution in pharmaceutically acceptable carriers, is a serious problem in the formulation of topical therapeutic products for the treatment of medical conditions affecting the skin or mucosa. Such lack of solubility is additionally a concern in the formulation of medications for parenteral administration and for oral liquids that are often used for children and geriatric patients. Accordingly, a significant need exists for a method to increase the solubility of drugs that are poorly soluble in water, and especially those, like azole drugs such as metronidazole, that are also poorly soluble in pharmaceutical oils.

DESCRIPTION OF THE INVENTION

It has been unexpectedly discovered that the combination of any two of a polyol, a polyol ether, and a low carbon organic alcohol provides a synergistic effect that produces an increase in the aqueous solubility of poorly water soluble compounds such as drugs, including poorly water soluble compounds, such as azole drugs.

As used herein, the term "poorly soluble" when referring to a chemical compound in relation to its solubility in water or an oil means a chemical compound that is sparingly soluble, slightly soluble, very slightly soluble, or insoluble in water or an oil, as defined in U.S. Pharmacopeia and National Formulary (USP-NF). According to this definition, solubility is stated in terms of the parts of the solvent needed to dissolve one part of the solute. A compound that is sparingly soluble in a particular solvent, such as water, requires 30-100 parts of the solvent to dissolve one part of the compound. A compound that is slightly solvent requires 100-1000 parts of the solvent. A compound that is very slightly soluble requires 1000-10,000 parts of the solvent. A compound that is insoluble requires more than 10,000 parts of the solvent to dissolve one part of the solute.

As used herein the term "polyol" is synonymous with "polyhydric alcohol" and refers to an alcohol that contains more than one hydroxyl group. Examples of polyols include polyether glycols, propylene glycol, and sugar alcohols.

As used herein, the term "polyol ether" refers to an alcohol that contains more than one hydroxyl group and an ether group. Examples of polyol ethers include diethylene glycol monoethyl ether (ethoxydiglycol) (Transcutol®, Gattefosse Corporation, Paramus, N.J.), ethers of pentaerythritol, ethers of alkylene glycol, ethers of a fatty alcohol, and ethers of a sugar.

As used herein, the term "low carbon organic alcohol" refers to an alcohol having the formula $RCH_2OH$, wherein R is either H or is a straight or branched alkyl chain of 1 to 7 carbons, or having a ring structure directly connected to a hydroxyl group or connected to a hydroxyl group by a carbon. Examples of low carbon organic alcohols include alkyl and aryl alcohols such as ethyl alcohol, propyl alcohol, isopropyl alcohol, phenol, and benzyl alcohol.

An example of such a poorly water soluble compound that is poorly soluble in pharmaceutical oils is the drug metronidazole, a member of the azole family of medications. This drug is utilized as an illustration of the invention. However, it will be understood that the description of the invention herein pertains not just to metronidazole but to all members of the azole family of medications, for example, fluconazole, ketoconazole, itraconazole, miconazole, dimetridazole, secnidazole, ornidazole, timidazole, camidazole, and panidazole.

In accordance with the invention, a polyol and a polyol ether, a polyol and a low carbon organic alcohol, a polyol ether and a low carbon organic alcohol, or a polyol, a polyol ether, and a low carbon organic alcohol are combined in an aqueous fluid with a poorly water soluble chemical azole compound, such as metronidazole to form an aqueous solution. The total concentration of the polyol and the polyol ether, the polyol and the low carbon organic alcohol, the polyol ether and the low carbon organic alcohol, or the polyol, the polyol ether, and the low carbon organic alcohol that is combined in the aqueous fluid is that which is sufficient to provide a synergistic increase in the solubility of the azole chemical compound in the aqueous fluid in the absence of any two or more of a polyol, a polyol ether, and a low carbon organic alcohol.

The absolute and relative concentrations of the polyol, polyol ether, and low carbon organic alcohol in the aqueous fluid may be varied, if desired, in order to obtain a particular increase in solubility of the azole compound in the aqueous fluid. It is expected, however, that any amount and any ratio of two or more of a polyol, polyol ether, and low carbon organic alcohol will result in a synergistic increase in solubility of azole compounds in the mixed solvent system compared to the solubility of the azole compounds in an aqueous fluid lacking two or more of a polyol, a polyol ether, and a low carbon organic alcohol.

The aqueous fluid may contain, in addition to the above components, additional components such as, but not limited to, additional solubility enhancing agents such as one or more of a cyclodextrin, niacin, and niacinamide, gelling agents such as a carbomer or a cellulosic polymer, preservatives, chelating agents, pH adjusting agents, and buffers.

The aqueous solution of the invention may constitute the internal aqueous phase of a water-in-oil emulsion or the external aqueous phase of an oil-in-water emulsion. Methods of making such emulsions are well known in the art.

The solutions of the invention, including gels, may be used for the topical treatment of dermatologic or mucosal disorders that are responsive to therapy with azole compounds such as metronidazole. In accordance with the method of treatment of the invention, a stable aqueous solution as described herein containing an azole compound and two or more of a polyol, a polyol ether, and a low carbon organic alcohol is topically applied to skin or mucosal surfaces in need of such therapy. Examples of disorders that are suitably treated in accordance with the invention include inflammatory lesions on skin or mucosa, such as oral or vaginal mucosa, diabetic foot ulcers, and certain infectious diseases that are responsive to topical therapy. A particular disorder that may be treated with the method of the invention is rosacea, also known as acne rosacea.

Preferably, the dissolved concentration of the azole compound in the pharmaceutical formulation of the invention is sufficient so that application once daily is effective to ameliorate the disorder. For example, with metronidazole, concentrations of about 1% or higher provide effective treatment when applied only once daily. At concentrations below 1.0%, it is recommended to apply a metronidazole formulation at least twice daily. The solution containing metronidazole or other azole compound is applied on a daily basis, one or more times per day, for a time sufficient to produce an amelioration or a cure of the disorder. In certain chronic disorders, the solution may be applied one or more times daily for a prolonged period to prevent worsening of the disorder.

The invention is further illustrated, in the following non-limiting examples. In the examples, propylene glycol is utilized as a representative polyol, Transcutol® is utilized as a representative polyol ether, benzyl alcohol is utilized as a representative low carbon organic alcohol, and metronidazole is utilized as a representative azole chemical compound it is understood, however, that other polyols, polyol ethers, low carbon organic alcohols, and azole compounds may be substituted in place of the exemplified propylene glycol, Transcutol®, benzyl alcohol, and metronidazole.

Example 1

Procedure for Determining Solubility of Metronidazole

In the Examples that follow, solubility of metronidazole was determined as follows.

An appropriate amount of each vehicle component was weighted into a 20 ml scintillation vial and the components were shaken until a clear solution was obtained. Metronidazole Was then added to the solution and the vials were Shaken overnight at room temperature to obtain a saturated solution of metronidazole. The solution was filtered to remove any undissolved metronidazole and the concentration of metronidazole dissolved in the solution was determined by HPLC. The solutions were physically stable at room temperature for at least two weeks, with no precipitation formation.

Example 2

Solubility of Metronidazole in Single Vehicles

The procedure of Example 1 was performed to determine the solubility of metronidazole in a single vehicle solvent selected from water, ethoxydiglycol, benzyl alcohol, and propylene glycol. The results are shown below in Table 1.

TABLE 1

| Solvent | Metronidazole Solubility % w/w |
|---|---|
| Water | 0.87 |
| Ethoxydiglycol | 2.47 |
| Benzyl Alcohol | 6.23 |
| Propylene Glycol | 1.88 |

Example 3

Solubility of Metronidazole in Multiple Vehicle System Containing Water, a Polyol, a Polyol Ether, and a Low Carbon Organic Alcohol The procedure of Example 1 was performed to determine the solubility of metronidazole in a multiple vehicle solvent system containing water, ethoxydiglycol, benzyl alcohol, and propylene glycol. The composition of the solvent system is shown below in Table 2.

TABLE 2

| Components | Amount % w/w |
|---|---|
| Ethoxydiglycol | 29.8 |
| Benzyl Alcohol | 5.0 |
| Propylene Glycol | 10.0 |
| Water | 55.2 |

Based on the solubility of metronidazole in each component of the multi-component vehicle system, the anticipated solubility of metronidazole in this vehicle was calculated to be 1.716% w/w. The calculations are shown in Table 3, where the solubility of each component in isolation tunes the concentration in the vehicle blend provides the anticipated (additive or calculated) solubility.

TABLE 3

| Component | Fractional Amount | Metronidazole solubility in individual component % | Anticipated solubility, % w/w |
|---|---|---|---|
| Ethoxydiglycol | 0.298 | 2.47 | 0.736 |
| Benzyl Alcohol | 0.050 | 6.23 | 0.312 |
| Propylene Glycol | 0.100 | 1.88 | 0.188 |
| Water | 0.552 | 0.87 | 0.480 |
| Total | 1.000 | | 1.716 |

Although, as shown in Table 3, the anticipated solubility of metronidazole in the multiple vehicle system was calculated to be 1.716% w/w, the actual solubility of metronidazole in this multi-component vehicle system was experimentally determined, by HPLC, to be 2.54% w/w, see Table 6, Blend #1, in Example 5 below. The solubility of metronidazole in the multi-component vehicle system was 48.5% higher than expected if the contribution to solubility by each of the components was additive. Thus, the results of this study establish that the combination of water, polyol, polyol ether, and low carbon organic alcohol provides a synergistic effect on the solubility of metronidazole in an aqueous vehicle.

Example 4

Solubility of Metronidazole in Multi-Component Vehicle System Containing Water, a Polyol, a Polyol Ether, and a Low Carbon Organic Alcohol The procedure of Example 3 was repeated except that the concentration of benzyl alcohol in the aqueous fluid was reduced by 50% and the concentration of water in the fluid was increased accordingly. The composition of the solvent system is shown in Table 4.

TABLE 4

| Components | Amount % w/w |
| --- | --- |
| Ethoxydiglycol | 29.9 |
| Benzyl Alcohol | 2.5 |
| Propylene Glycol | 10.1 |
| Water | 57.5 |

Based on the solubility of metronidazole in each component of the multiple vehicle system, the anticipated solubility of metronidazole in this system was calculated to be 1.582% w/w. The calculations are shown in Table 5.

TABLE 5

| Component | Fractional Amount | Metronidazole solubility in individual | Anticipated solubility % w/w |
| --- | --- | --- | --- |
| Ethoxydiglycol | 0.299 | 2.47 | 0.739 |
| Benzyl Alcohol | 0.025 | 6.23 | 0.156 |
| Propylene Glycol | 0.101 | 1.88 | 0.190 |
| Water | 0.575 | 0.87 | 0.500 |
| Total | 1.000 | | 1.584 |

In the solution containing the components shown in Table 4, the solubility of metronidazole in the multi-component vehicle system was experimentally determined, by HPLC, to be 2.07% w/w, see Table 6, Blend #2, in Example 5 below. The solubility of metronidazole in this multi-component vehicle system was 31.0% higher than expected if the contribution solubility by each of the components was additive.

Example 5

Solubility of Metronidazole in a Variety of Concentrations of the Multi-Component Solvent System The procedure of Example 1 was utilized to create a variety of multi-component solvent systems containing water, a polyol, a polyol ether, and a low carbon organic alcohol. The anticipated calculated solubility of metronidazole in each system was calculated and the actual solubility of metronidazole in each system was determined by HPLC as described, in Example 1. Blends #1 and 2 are the solvent systems of Examples 3 and 4, respectively. The results are shown in Table 6.

TABLE 6

| Blend # | Water | Transcutol ® | Benzyl alcohol | Propylene glycol | Theoretical Solubility (% w/w)[1] | Actual Solubility (% w/w)[2] | Solubility Increase %[3] |
| --- | --- | --- | --- | --- | --- | --- | --- |
| 1 | 55.2 | 29.8 | 5.0 | 10.0 | 1.71 | 2.54 | 48.5* |
| 2 | 57.5 | 29.9 | 2.5 | 10.1 | 1.58 | 2.07 | 31.0* |
| 3 | 60.0 | 30.0 | 0.0 | 10.0 | 1.45 | 1.66 | 14.5* |
| 4 | 65.1 | 29.9 | 0.0 | 5.0 | 1.4 | 1.48 | 5.7 |
| 5 | 65.0 | 30.0 | 5.0 | 0.0 | 1.62 | 2.27 | 40.1* |
| 6 | 71.0 | 29.0 | 0.0 | 0.0 | 1.33 | 1.35 | 1.5 |
| 7 | 73.1 | 16.9 | 0.0 | 10.0 | 1.24 | 1.22 | (1.6) |
| 8 | 74.1 | 16.0 | 5.0 | 5.0 | 1.44 | 1.96 | 36.1* |
| 9 | 74.5 | 12.9 | 2.5 | 10.1 | 1.31 | 1.54 | 17.6* |
| 10 | 74.9 | 23.0 | 2.1 | 0.0 | 1.35 | 1.66 | 23.0* |
| 11 | 81.4 | 11.1 | 2.5 | 5.0 | 1.23 | 1.43 | 16.3* |
| 12 | 83.9 | 1.1 | 5.1 | 10.0 | 1.26 | 1.72 | 36.5* |
| 13 | 84.9 | 0.0 | 5.1 | 10.0 | 1.24 | 1.66 | 33.9* |
| 14 | 89.0 | 11.0 | 0.0 | 0.0 | 1.04 | 1.01 | (2.9) |
| 15 | 89.9 | 0.0 | 0.0 | 10.1 | 0.97 | 0.93 | (4.1) |
| 16 | 91.5 | 3.4 | 5.1 | 0.0 | 1.2 | 1.56 | 30.0* |
| 17 | 92.5 | 0.0 | 2.5 | 5.1 | 1.05 | 1.20 | 14.3* |
| 18 | 95.0 | 0.0 | 0.0 | 5.0 | 0.92 | 0.91 | (1.1) |
| 19 | 95.0 | 0.5 | 4.5 | 0.0 | 1.12 | 1.44 | 28.6* |
| 20 | 97.6 | 0.0 | 2.4 | 0.0 | 1.00 | 1.09 | 9.0 |

[1]Theoretical (anticipated) solubility is based on the assumption that each solvent's contribution to overall solubility is additive and is calculated from the determined solubility of metronidazole due to each component as shown in Table 1 in Example 2
[2]Actual solubility of metronidazole was obtained by HPLC analysis
[3]Actual solubility minus theoretical solubility divided by theoretical solubility and multiplied by 100.
*Solubility increase or (decrease) greater than +/−10% is considered to be significant The data in Table 6 establishes the synergism obtained by combination of any two of a polyol, a polyol ether, and a low carbon organic alcohol. The highest percentage increases in solubility were obtained in solvent systems that included a low carbon organic alcohol. No increase in solubility above the calculated solubility was obtained when utilizing a solvent system containing water and only one other solvent.

Example 6

Metronidazole 1.5% Gel

An exemplar gel pharmaceutical composition containing metronidazole at a concentration of 1.5% w/w was produced by combining the following components, as shown below in Table 7.

TABLE 7

| Components | % w/w |
|---|---|
| Metronidazole | 1.50 |
| Propylene glycol | 5.00 |
| Niacinamide | 3.00 |
| Beta-Cyclodextrin | 1.00 |
| Methylparaben | 0.15 |
| Propylparaben | 0.05 |
| EDTA disodium | 0.05 |
| Transcutol ® P | 15.00 |
| Benzyl alcohol | 1.00 |
| Carbopol ® Ultrez 10 | 0.50 |
| 25% Triethanolamine | q.s. pH 6.0 |
| 10% HCl solution | q.s. pH 6.0 |
| Purified water | q.s. 100.00 |

The gel composition was made by combining metronidazole, propylene glycol, niacinamide, beta-cyclodextrin, methylparaben propylparaben EDTA disodium, Transcutol® P, and benzyl alcohol in a manufacturing vessel. These components were mixed while, heating to 65° C. until a clear solution was obtained. After removal from the heat source, the gelling agent, Carbopol® Ultrez 10 (Lubrizol Corp., Wickliffe, Ohio) was added with continuous mixing until dispersed into the mixture. Mixing was continued until a homogenous gel was formed and the system reached room temperature. The pH was then adjusted to 6.0+/−0.3 with triethanolamine or HCl solution.

Example 7

Metronidazole 1.25% and 1.5% Gels

Exemplary gel pharmaceutical compositions containing metronidazole at a concentration of 1.25% w/w and 1.5% w/w were produced according to the method of Example 6 by combining the following components, as shown below in Tables 8 and 9, respectively. The solutions were determined to be stable with no evidence of precipitate formation following storage at room temperature for two weeks or at a temperature of 5° C. for one week.

TABLE 8

| Components | % w/w |
|---|---|
| Metronidazole | 1.25 |
| Propylene glycol | 5.00 |
| Methylparaben | 0.15 |
| Propylparaben | 0.05 |
| EDTA sodium | 0.05 |
| Ethoxydiglycol | 25.00 |
| Benzyl alcohol | 1.00 |
| Carbopol ® Ultrez 10 | 0.50 |
| 25% Triethanolamine | q.s. pH 6.0 |
| 10% HCl solution | q.s. pH 6.0 |
| Purified water | q.s. 100.00 |

TABLE 9

| Components | % w/w |
|---|---|
| Metronidazole | 1.50 |
| Propylene glycol | 10.00 |
| Methylparaben | 0.15 |
| Propylparaben | 0.05 |
| EDTA sodium | 0.05 |
| Ethoxydiglycol | 25.00 |
| Benzyl alcohol | 2.00 |
| Carbopol ® Ultrez 10 | 0.50 |
| 25% Triethanolamine | q.s. pH 6.0 |
| 10% HCl solution | q.s. pH 6.0 |
| Purified water | q.s. 100.00 |

Example 8

Metronidazole 1.25% and 1.5% Gels

Exemplary gel pharmaceutical compositions containing metronidazole at a concentration of 1.25% w/w and 1.5% w/w were produced according to the method of Example 6 by combining the following components, as shown below in Tables 10 and 11, respectively. The solutions were determined to be stable with no evidence of precipitate formation following storage at room temperature for to weeks or at a temperature of 5° C. for one week.

TABLE 10

| Components | % w/w |
|---|---|
| Metronidazole | 1.25 |
| PEG 400 | 5.00 |
| Methylparaben | 0.15 |
| Propylparaben | 0.05 |
| EDTA sodium | 0.05 |
| Ethoxydiglycol | 35.00 |
| Ethanol | 3.00 |
| Carbopol ® Ultrez 10 | 0.50 |
| 25% Triethanolamine | q.s. pH 6.0 |
| 10% HCl solution | q.s. pH 6.0 |
| Purified water | q.s. 100.00 |

TABLE 11

| Components | % w/w |
|---|---|
| Metronidazole | 1.50 |
| Hexylene glycol | 5.00 |
| Methylparaben | 0.15 |
| Propylparaben | 0.05 |
| EDTA sodium | 0.05 |
| Ethoxydiglycol | 35.00 |
| Ethanol | 3.00 |
| Carbopol ® Ultrez 10 | 0.50 |
| 25% Triethanolamine | q.s. pH 6.0 |
| 10% HCl solution | q.s. pH 6.0 |
| Purified water | q.s. 100.00 |

Various modifications of the above described invention will be evident to those skilled in the art. It is intended that such modifications are included within the scope of the following claims.

The invention claimed is:

1. A pharmaceutical composition comprising water and at least about 1.25% w/w metronidazole to about 1.5% w/w metronidazole, wherein the composition further comprises at least two of a polyol, a polyol ether, and a low carbon organic alcohol.

2. The composition of claim 1 wherein the low carbon organic alcohol is benzyl alcohol.

3. The composition of claim 2 wherein the benzyl alcohol comprises about 1% w/w of the composition.

4. The composition of claim 2 wherein the benzyl alcohol comprises about 2% w/w of the composition.

5. The composition of claim 1 wherein the polyol is propylene glycol.

6. The composition of claim 1 wherein the polyol ether is an ether of an alkylene glycol.

7. The composition of claim 6 wherein the ether of the alkylene glycol is polyethylene glycol.

8. The composition of claim 7 wherein the polyethylene glycol is polyethylene glycol 400 ("PEG 400").

9. The composition of claim 1 wherein the water comprises about 55% or more w/w of the composition.

10. The composition of claim 1 wherein the composition comprises each of a polyol, a polyol ether, and a low carbon organic alcohol.

* * * * *